United States Patent
Bernhardt et al.

(10) Patent No.: US 7,372,935 B2
(45) Date of Patent: May 13, 2008

(54) METHOD FOR MINIMIZING IMAGE ARTIFACTS AND MEDICAL IMAGING SYSTEM

(75) Inventors: Philipp Bernhardt, Forchheim (DE); Jan Boese, Eckental (DE); Marcus Pfister, Bubenreuth (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/435,186

(22) Filed: May 16, 2006

(65) Prior Publication Data
US 2006/0262894 A1 Nov. 23, 2006

(30) Foreign Application Priority Data
May 17, 2005 (DE) .................. 10 2005 022 540

(51) Int. Cl.
*A61B 6/03* (2006.01)
(52) U.S. Cl. .................. 378/4; 378/63; 378/901
(58) Field of Classification Search .................. 378/4, 378/197, 198, 8, 63, 901; 600/407, 427; 356/601
See application file for complete search history.

(56) References Cited

U.S. PATENT DOCUMENTS

| | | | | |
|---|---|---|---|---|
| 4,888,693 | A * | 12/1989 | Tam | 378/4 |
| 4,920,491 | A * | 4/1990 | Eberhard et al. | 382/131 |
| 5,270,926 | A * | 12/1993 | Tam | 378/4 |
| 5,463,721 | A * | 10/1995 | Tam | 345/427 |
| 5,611,026 | A * | 3/1997 | Eberhard et al. | 345/419 |
| 6,466,638 | B1 * | 10/2002 | Silver et al. | 378/4 |
| 6,574,296 | B2 * | 6/2003 | Stierstorfer | 378/15 |
| 6,590,669 | B1 | 7/2003 | Wagner | |
| 6,631,284 | B2 | 10/2003 | Nutt et al. | |
| 6,937,696 | B1 * | 8/2005 | Mostafavi | 378/95 |
| 2002/0045817 | A1 * | 4/2002 | Ichihashi | 600/425 |
| 2004/0254456 | A1 * | 12/2004 | Ritter | 600/425 |
| 2004/0258210 | A1 * | 12/2004 | Ritter | 378/198 |
| 2007/0238957 | A1 * | 10/2007 | Yared | 600/407 |

FOREIGN PATENT DOCUMENTS

| | | |
|---|---|---|
| DE | 102 58 130 A1 | 6/2004 |
| DE | 103 17 137 A1 | 11/2004 |
| EP | 0 372 241 B1 | 6/1990 |

OTHER PUBLICATIONS

Moring et al., Acquisition of three-dimensional image data by a scanning laser range finder, Aug. 1989, Optical Engineering, vol. 28, No. 8, pp. 897-902.*
Gruber et al., Simple, robust and accurate phase-measuring triangulation, Optik, 1992, vol. 89, No. 3, pp. 118-122.*

(Continued)

*Primary Examiner*—Edward J. Glick
*Assistant Examiner*—John M Corbett

(57) ABSTRACT

The invention relates to a method for "truncation correction" in an x-ray system, i.e. a correction method during the reconstruction of projection images of an object recorded from different projection angles, if parts of the object do not lie in the field of view of each projection image. The surface of the object is thereby optically detected and used during the reconstruction of projection images to supplement the missing image data.

20 Claims, 2 Drawing Sheets

OTHER PUBLICATIONS

Englelhardt et al., Acquisition of 3-D data by focus sensing, Applied Optics, Nov. 15, 1988, vol. 27, No. 22, pp. 4684-4689.*

Ramesh R.Galigekere and David W. Holdsworth; "3D Reconstruction from Truncated Rotational Angiograms Using Linear Prediction"; Proceedings of MICCAI; 2003, pp. 126-133.

B.Ohnesorge, T. Flohr, K. Schwarz, J.P. Heiken, K.T. Bae; "Efficient Correction for CT Image Artifacts Caused by Objects Extending Outside the Scan Field of View"; Medical Physics; Jan. 2000; pp. 39-46; vol. 27, No. 1.

* cited by examiner

METHOD FOR MINIMIZING IMAGE ARTIFACTS AND MEDICAL IMAGING SYSTEM

CROSS REFERENCE TO RELATED APPLICATIONS

This application claims priority of German application No. 10 2005 022 540.3 filed May 17, 2005, which is incorporated by reference herein in its entirety

FIELD OF THE INVENTION

The invention relates to a method for minimizing image artifacts during the reconstruction of tomography images of an object from several projection images of the object recorded from different projection angles, as well as a medical imaging system. The said image artifacts are those that are produced as a result of parts of the examined object thereby not lying in the field of view of each projection image (so-called measuring field overshoot).

BACKGROUND OF THE INVENTION

With x-ray computed tomography for medical use, a three-dimensional image of the object is calculated by means of a specific method from standard x-ray images, which contain no depth information since they display a projection of a three-dimensional object on a two-dimensional plane. The x-ray tube and detector are hereby rotated about the object through at least 180° and projection images of the object are thereby recorded in small angular steps. A three-dimensional data set of the object can be achieved from these numerous projection images by means of special algorithms, e.g. the so-called filtered back projection. This imaging method is generally carried out using computed tomographs (CT) specially designed for this purpose.

Other x-ray devices allowing good access to the patient are often used for x-ray recordings during image-controlled diagnostic or surgical interventions on patients, in which standard x-ray images are continuously recorded during said intervention. The so-called C-arm systems, in which the x-ray tube and detector are arranged on opposing arms of a C-arm which can move freely about the patient, are favored here. Three-dimensional tomography images of the patient can optionally also be generated with such C-arm systems, since the C-arm can likewise move through approximately 180° about the patient. However the problem often arises here that the x-ray detector is relatively small, in particular smaller than with conventional computed tomographs, and thus parts of the object are truncated on some of the projection images, and therefore no longer lie in the field of view of each projection image. Artifacts result during the reconstruction of the projection images into a three-dimensional tomography image, since these parts of the object are in some projection images, but not others.

Methods to correct such truncated projection images (so-called "truncation correction") are proposed, which hereby essentially reduce the image artifacts, by reducing the stage at which the image intensity suddenly drops to zero by virtue of the end of the field of view. The truncated projection image is supplemented, e.g. by means of linear extrapolation or another slow drop in the image intensity to zero, and these supplemented projection images are used for the reconstruction. Methods of this type are disclosed for instance in B. Ohnesorge et al., "Efficient correction for CT image artifacts caused by objects extending outside the scan field of view, "Med. Phys., vol. 27, no. 1, pp. 39-46, 2000 und R. R. Galigekere and D. W. Holsworth, "3D Reconstruction from Truncated Rotational Angiograms using Linear Prediction of view", Proceedings of MICCAI 2003 pp. 126-133, 2003, as well as in the references of this article. These methods allow the image artifacts to be reduced, but an optimal correction is however not possible.

SUMMARY OF THE INVENTION

The object of the invention is thus to provide a method and an imaging system, by means of which the artifacts can be minimized, which are produced as a result of parts of the object being truncated in some projection images.

The invention achieves this with the features of the claims. Preferred embodiments of the invention are specified in the respective dependent claims.

In accordance with the claimed method, the surface of the examined object, e.g. of the patient, is detected with the aid of an optical sensor. This optically detected surface is then used during the reconstruction of the projection images in order to supplement the missing image data.

The invention is based on the knowledge that the reconstruction of truncated projection images can be considerably improved if the size of the truncated part of the object and the external shape thereof is known. It is however not yet known which image density, i.e. if the projection images are x-ray recordings, has which x-ray absorption properties of this part of the object. This can, however, be estimated according to a preferred embodiment. With x-ray images, the assumption that the truncated part comprises water-equivalent material delivers good results. According to another embodiment, the x-ray absorption properties of the part of the object mapped in the projection image can be extended to the truncated part.

During the reconstruction of the projection images, the external limits of the object are preferably reconstructed outside the field of view on the basis of the optically detected surface.

A surface model is advantageously created from the detected surface of the object, said surface model being used during the reconstruction in place of the measured surface. This reduces the computing time, since the surface model models the surface as a series of triangles for instance and thus features a lower data density.

The invention also focuses on a medical imaging system, which features an optical sensor for detecting the surface of an object as well as a computing means for reconstructing the projection images into tomography images, with the detected surface of the object being used to supplement the missing image data. The reconstruction can be carried out according to the method described above.

The medical imaging system is preferably an x-ray C-arm system, which comprises an x-ray tube and an x-ray detector, which are fixed to a C-arm, which can be moved about the object, in particular about the patient. The preferred embodiments of the invention are described below with reference to C-arm systems, but the invention can however also be used correspondingly with computed tomographs.

The optical sensor used to detect the surface is preferably also fixed to the C-arm. Alternatively, the optical sensor can however also be arranged in a stationary or mobile manner in the examination room, e.g. fixed permanently to the ceiling or on a moveable stand.

The coordinate system of the C-arm and that of the optical sensor are preferably calibrated spatially to one another so that the spatial relationship between the detected surface of the object and the projection images of the object is known. If the optical sensor is fixed to the C-arm, a calibration of this type can be carried out during the production of the imaging system, otherwise such a calibration can be carried out prior to the projection images being recorded. If the coordinate systems of the optical sensor and the imaging system are not calibrated to one another, it is also possible to register the detected surface or the surface model of the object spatially with the recorded projection images of the object, in other words to determine the spatial relationship between recorded projection images and the surface after the event. Any registration method known in the prior art can be used for this purpose to superimpose the recorded projection images onto the surface model directly or indirectly. The following "double reconstruction method" is however particularly preferably used. Preliminary tomography images of the object are hereby reconstructed from the recorded projection images, with one of the known methods being able to be used to correct truncated projection images. The surface of the object is extracted from these preliminary images, e.g. also as a triangular model. This surface or this model is then registered spatially with the surface detected by the optical sensor or the corresponding surface model by means of a 3D-3D registration. 3D-3D registration methods of this type are known to the person skilled in the art. The size and shape of the object parts lying outside the field of view are hereby known. With this knowledge and optionally a statistical assumption about the x-ray absorption behavior of the truncated parts, a refined reconstruction with an improved "truncation correction" can now be carried out.

Different methods can be applied for optical surface detection. The optical sensor preferably comprises a light source and at least one camera. Optical sensors of this type are available from 3D-SHAPE GmbH and are based on the projection of striped patterns. The patterns are projected onto the object to be detected by means of a projector from a first direction and are viewed from another direction with a camera. The stripes appear more or less deformed to the camera, depending on the shape of the viewed object. The shape of the object can also be concluded from the deformation of the stripes. Generally more than 3 striped patterns are projected, with the intensity of the stripes assuming a sinusoidal pattern. A second camera can be provided to detect two sides of the object simultaneously.

This method for optical surface detection, also known as shape detection, is described in DE 102 58 130 A1 for instance. This publication, the disclosure of which is herewith included in this patent application, also describes a method, which is referred to as "shape from shading". With this method, the shape of the mapped object is concluded from the variation in the brightness in an image. If the photograph of a face is examined for instance, brightness variations are determined, although it can be assumed that the reflection coefficient of the skin hardly changes. Rather these brightness variations result from certain parts of the surface being oriented in such a way that they radiate more light to the camera than others. If the light from a light source strikes the surface at a right angle, the brightness is at a maximum, while with glancing incidence it is at a minimum. The contour can be determined from these differences.

Further methods for the optical shape detection of objects are described in U.S. Pat. No. 6,590,669 and EP 0 372 241 B1. Any suitable optical sensor system and/or method for optical surface detection can, in principle, be used for the present imaging system and collision protection method. The above-mentioned system from 3D-SHAPE GmbH, with which the object to be measured, in this instance the patient, is illuminated with a striped pattern (see www.3D-shape-.com), is particularly preferable. As only a relatively rough resolution of the measured surface is required for the purpose of the present application, the patient surface can be detected in a period of one or a few seconds up to approximately one minute.

If the surface detection is rapid enough, it can also be used to identify whether significant patient movement took place during the recording. Since the recordings can not be used in this case for tomographical reconstruction, it is expedient to interrupt the recording so as to reduce the radiation dose.

BRIEF DESCRIPTION OF THE DRAWINGS

Preferred exemplary embodiments of the invention are described below by way of example on the basis of the accompanying drawings, in which.

DETAILED DESCRIPTION OF THE INVENTION

Figure 1:
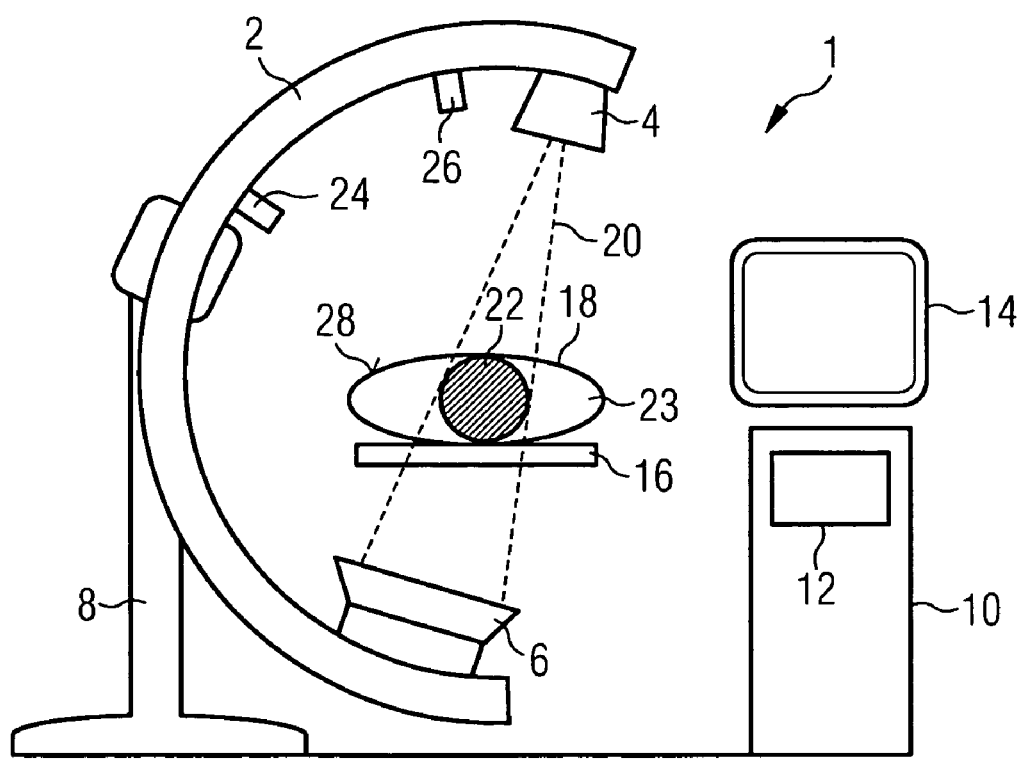
FIG. 1 shows a schematic view of a C-arm system, which is suited to executing an exemplary embodiment of the method according to the invention.

The invention is described below using the example of an x-ray C-arm system, in which the x-rayed region 22 is smaller than the patient 18. A C-arm system 1 of this type is shown schematically in FIG. 1. The x-ray tube 4 and the x-ray detector 6 are fixed here to opposing ends of a C-arm 2. This C-arm is in turn suspended in a moveable manner on a stand 8 and can thus be moved freely about a patient support 16. The rotation of the C-arm 2 about the support 16 allows a patient 18 lying thereupon to be x-rayed from different projection angles. The beam path of the fan-shaped or tapered x-ray beam is indicated with 20. The drawing clearly shows that the detector 6 is not large enough to record an image of the whole patient 18. Rather a part 23 of the patient does not lie within the x-ray fan.

Figure 2:
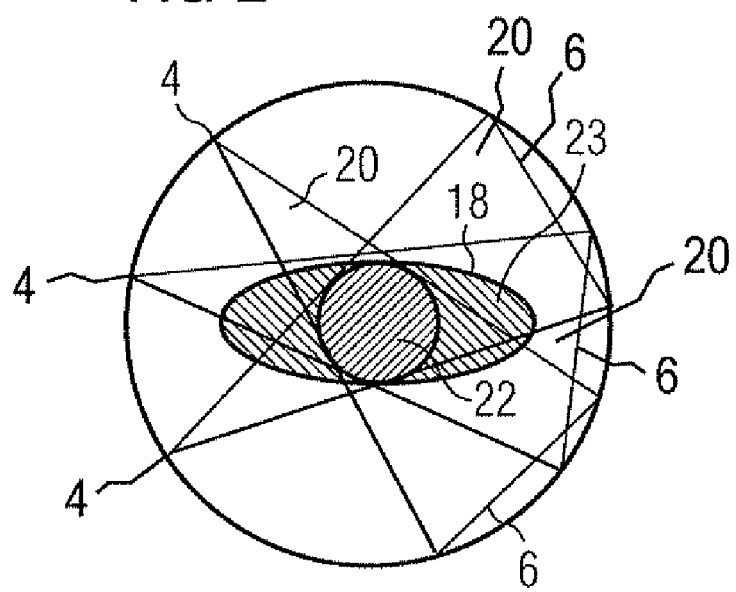
FIG. 2 shows a schematic cross-section through an x-ray system with a patient.

This problem of the measuring field overshoot is shown even more clearly in FIG. 2. In the centre, the cross-section of the patient 18 is shown schematically as an ellipsoid. Furthermore three fans 20 are shown by way of example, which extend from an x-ray tube 4 to an x-ray detector 6. It is clear that only the smaller area 22 actually lies in all the x-ray beam fans. The outer area 23 is however truncated at least on one (not all) projection image(s). Only incomplete scanning values thus exist for this measuring field overshoot, rendering the reconstruction problem generally 'incomplete'.

Reverting to FIG. 1, a camera 26 and a projector 24 are further fixed to the C-arm in order to resolve this problem. These two devices, which together form the optical sensor, can alternatively also be arranged for instance on the ceiling of the examination room or at another point with a free view of the patient. As described further above, the projector 24 radiates the patient 18 with an optical striped pattern. The distortion of this striped pattern is detected by the camera 26 and used to measure the shape of the surface 28 of the patient. In the example shown, the optical sensor can be rotated about the patient together with the C-arm 2, so as to record its surface 28 from all sides.

By registering this detected surface 28 with the coordinate system of the C-arm, the size and shape of the measuring field overshoot 23, in other words the parts of the patient, which do not lie in the field of view of each projection image, can be precisely determined. Certain assumptions of the x-ray absorption properties of this tissue, e.g. from the other projections or by assuming water equivalent properties, allow the reconstructed tomography images to be optimally corrected. The reconstruction is carried out for instance in the computing module 12 of the control computer 10 of the C-arm system. The corrected tomography images can then be displayed on a screen 14.

Figure 3:
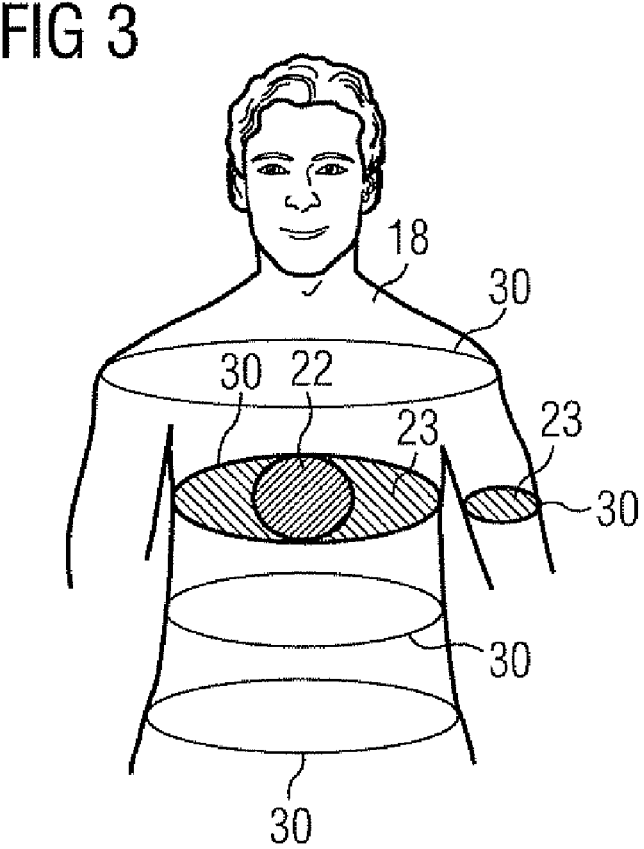
FIG. 3 shows a schematic view of a patient with a surface model.

According to a preferred embodiment, a surface model of the patient is created from the detected surface. This is shown by way of example in FIG. 3, in which the periphery of a patient 18 is modeled in each instance in a simplified manner by ellipsoids 30. The inner area 22 to be reconstructed is shown by way of example within one of the ellipsoids. The area of the measuring field overshoot 23 extends on the one hand inside the torso of the patient. Furthermore, the diameter of the arm can also be detected by means of surface detection and the surface of said arm can be modeled by a further ellipse 30, which likewise comprises a truncated part of the patient. The measured image data can thus be expediently supplemented by the surface spanned by the ellipses 30, by making assumptions about the absorption properties in this area at the same time.

The invention thus succeeds in proposing a rapid, accurate and simple option for "truncation correction".

The invention claimed is:

1. A method for minimizing an image artifact during a reconstruction of a plurality of projection images into a tomography image of an object, comprising:
    recording the plurality of projection images of the object from a plurality of projection angles;
    detecting a surface of the object with an optical sensor;
    creating a surface model of the object from the optically detected surface;
    supplementing missing data from the projection images based on the surface model of the object during the reconstruction of the projection images into the tomography image of the object; and
    using the tomography image of the object in a humanly perceptible manner,
    wherein the artifact is a result of a part of the object which is not in a field of view of each of a projection image.

2. The method as claimed in claim 1,
    wherein an external limit of the object outside the field of view is reconstructed based on the optically detected surface during the reconstruction of the project images,
    wherein an image density of the object outside the field of view is estimated based on an image density measured in the projection images during the reconstruction of the project images.

3. The method as claimed in claim 1, wherein the surface model of the object models the surface as a series of triangles.

4. The method as claimed in claim 1, wherein the projection images are recorded using an x-ray system.

5. The method as claimed in claim 4, wherein the x-ray system is a C-arm system or a computed tomography.

6. The method as claimed in claim 4, wherein coordinate systems of the optical sensor and the x-ray system are calibrated spatially with respect to each other.

7. The method as claimed in claim 1, wherein the surface model of the object is registered spatially with the recorded projection images of the object comprising:
    a preliminary tomography image of the object is reconstructed from the recorded projection images,
    a surface of the object is extracted from the preliminary tomography image, and
    the surface extracted from the preliminary tomography image and the surface model are registered spatially with respect to each other by a 3D-3D registration.

8. The method as claimed in claim 7, wherein the 3D-3D registration is used to superimpose the recorded projection images onto the surface model.

9. The method as claimed in claim 1, wherein the surface is detected a plurality of times by the optical sensor during a recording of the projection images and the recording is interrupted if the detected surface changes as a result of a movement of the object during the recording.

10. The method as claimed in claim 1, wherein the optical sensor comprises a camera and a light source, the light source comprising a projector which illuminates the object with a striped pattern.

11. The method as claimed in claim 1, wherein the object is a human patient.

12. A medical imaging system for reconstructing a plurality of projection images into a tomography image of an object and minimizing an image artifact during the reconstruction, comprising:
    an optical sensor for detecting a surface of the object; and
    a computing device configured to create a surface model of the object from the optically detected surface and to supplement missing image data from the projection images using the surface model of the object for reconstructing the projection images into the tomography image,
    wherein the plurality of projection images of the object is recorded from a plurality of projection angles and the image artifact is a result from a part of the object which is not in a field of view of a projection image.

13. The medical imaging system as claimed in claim 12, wherein the optical sensor comprises a camera and a light source, the light source comprising a projector which illuminates the object with a striped pattern.

14. The medical imaging system as claimed in claim 12, wherein the surface model of the object models the surface as a series of triangles.

15. The medical imaging system as claimed in claim 12, wherein the medical imaging system further comprises an image recording system which is rotated about the object.

16. The medical imaging system as claimed in claim 15, wherein coordinate systems of the image recording system and the optical sensor are calibrated spatially with respect to each other.

17. The medical imaging system as claimed in claim 15,
    wherein the image recording system is a C-arm system containing an x-ray tube and an x-ray detector,
    wherein the x-ray tube and the x-ray detector are fixed to a C-arm of the C-arm system,
    wherein the C-arm is movable about the object.

18. The medical imaging system as claimed in claim 17, wherein the optical sensor is fixed to the C-arm.

19. The medical imaging system as claimed in claim 12, wherein the optical sensor is arranged in a stationary or mobile device within an examination room.

20. The medical imaging system as claimed in claim 12, wherein the object is a human patient.

* * * * *